(12) United States Patent
Klenner

(10) Patent No.: US 10,763,647 B2
(45) Date of Patent: Sep. 1, 2020

(54) GROUND CONTACT INTEGRATED INTO WELDING PROTECTION STRIP

(71) Applicant: BIOTRONIK SE & CO KG, Berlin (DE)

(72) Inventor: Rolf Klenner, Michendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 16/038,247

(22) Filed: Jul. 18, 2018

(65) Prior Publication Data

US 2019/0052065 A1 Feb. 14, 2019

(30) Foreign Application Priority Data

Aug. 9, 2017 (EP) .................................. 17185502

(51) Int. Cl.
| | |
|---|---|
| *A61N 1/375* | (2006.01) |
| *H01R 13/658* | (2011.01) |
| *H02B 1/16* | (2006.01) |
| *A61N 1/08* | (2006.01) |
| *H01R 4/66* | (2006.01) |
| *H02H 3/16* | (2006.01) |

(52) U.S. Cl.
CPC .............. *H02B 1/16* (2013.01); *A61N 1/08* (2013.01); *A61N 1/375* (2013.01); *A61N 1/37512* (2017.08); *H01R 4/66* (2013.01); *H01R 13/658* (2013.01); *H02H 3/16* (2013.01)

(58) Field of Classification Search
CPC .......... H01R 13/65802; H01R 13/6594; H01R 13/6595; H01R 13/65946; A61N 1/37512; A61N 1/375; A61N 1/08
See application file for complete search history.

(56) References Cited

U.S. PATENT DOCUMENTS

| | | | |
|---|---|---|---|
| 6,072,613 A * | 6/2000 | Henningsson | G02B 6/4246 361/748 |
| 6,257,905 B1 * | 7/2001 | Johnson | H01R 13/6485 174/541 |
| 6,979,502 B1 | 12/2005 | Gartstein et al. | |
| 8,968,919 B2 | 3/2015 | Caumont et al. | |
| 9,795,796 B2 * | 10/2017 | Bortolin | A61N 1/3752 |
| 2009/0289596 A1 * | 11/2009 | McGinley | H01R 31/065 320/111 |
| 2018/0151987 A1 * | 5/2018 | Zhao | H01R 13/506 |

* cited by examiner

*Primary Examiner* — Felix O Figueroa
(74) *Attorney, Agent, or Firm* — Laurence A. Greenberg; Werner H. Stemer; Ralph E. Locher

(57) ABSTRACT

An assembly contains a housing defining an internal space of the assembly, an electronic circuit arranged in the internal space, and a protection strip arranged in the internal space for protecting the electronic circuit against external influences. Accordingly, the protection strip forms a ground conductor that is electrically connected to the housing and to a ground connection of the electronic circuit. Furthermore, a method for producing the assembly is disclosed.

18 Claims, 2 Drawing Sheets

GROUND CONTACT INTEGRATED INTO WELDING PROTECTION STRIP

CROSS-REFERENCE TO RELATED APPLICATION

This application claims the priority, under 35 U.S.C. § 119, of European application EP 17185502.6, filed Aug. 9, 2017; the prior application is herewith incorporated by reference in its entirety.

BACKGROUND OF THE INVENTION

Field of the Invention

The present invention relates to an assembly, particularly in the form of an implantable medical device such as cardiac pacemaker, particularly an implantable leadless pacemaker (iLP) or a loop recorder.

Usually, an electronic circuit of such an assembly has to make electronic contact with a surrounding housing (ground potential).

In the prior art, such contacts are e.g. established by using a separate ground pin connected via a small wiring band to the circuit. As a consequence enough installation space has to be provided in order to fit this type of a connection into the housing of the assembly/medical device. Thus, less installation space is available for actual components of the circuit. Further, costs for such small wiring bands are not negligible. Furthermore, the handling of such wiring bands often leads to problems such as faulty electrical contacts and frequently requires time consuming manual correction/adjustment.

Furthermore, U.S. Pat. No. 8,968,919 B2 discloses welding strips that are used as electrical connection devices for contacting battery cells.

SUMMARY OF THE INVENTION

Based on the above, the problem to be solved by the present invention is to provide an improved way of providing an electrical connection between a ground connection of an electronic circuit and a housing enclosing the circuit.

This problem is solved by an assembly having the features of the main apparatus claim as well as by a method having the features of the main method claim. Preferred embodiments of these aspects of the present invention are stated in the corresponding sub claims and are described below.

With the foregoing and other objects in view there is provided, in accordance with the invention, an assembly, comprising:
a) a housing defining an internal space of the assembly,
b) an electronic circuit arranged in the internal space, and
c) a protection strip arranged in the internal space for protecting the electronic circuit against external influences.

Wherein according to the present invention, the protection strips forms a ground conductor that is electrically connected to the housing and to a ground connection of said electronic circuit.

Thus, the present invention integrates the function of electrically connecting the circuit to the housing into the already existing protection strip so that special components such as a separate ground pin and an associated wiring band can be omitted. Besides the fact that the number of parts is reduced also installation space is saved and can be used for further components of the actual circuit. Alternatively, the free installation space provides the possibility to further miniaturize the assembly.

Particularly, the assembly can be or can form part of a medical device, particularly an implantable medical device, a cardiac pacemaker, particularly an implantable leadless pacemaker (iLP), or a loop recorder etc.

Further, particularly, in an embodiment the protection strip is configured to protect the electronic circuit against temperature influences, particularly external heat (see also below).

Further, according to an embodiment of the assembly according to the present invention, the housing comprises two housing parts, particularly shells, wherein each housing part comprises a circumferential boundary area, wherein the boundary areas are connected to form the housing.

Furthermore, according to an embodiment of the assembly according to the present invention, the housing parts are connected via a welding seam that connects the boundary areas. The welding seam may be formed using laser welding or another suitable technique.

Further, according to an embodiment of the assembly according to the present invention, the protection strip is configured to protect the electronic circuit against external influences generated upon welding of the welding seam. Such influences can be heat that is generated by the welding process as well as welding material splatter.

Furthermore, according to an embodiment of the assembly according to the present invention, the protection strip is arranged such that in the internal space it overlaps with both boundary regions on an inside of the housing, which inside faces the electronic circuit.

Furthermore, according to an embodiment of the assembly according to the present invention, the protection strip comprises a wing protruding from an elongated portion of the protection strip that extends along the circumferential boundary area of the first housing part, which wing is particularly bent down towards the ground connection and connected, particularly welded, to the ground connection of the electronic circuit so that the wing stands in electrical contact with the ground connection.

Particularly, in an embodiment, the electronic circuit is arranged on a substrate, which can be formed by a printed circuit board (PCB). Particularly, the ground connection can be formed by a contact pad that is arranged on the substrate.

Further, particularly, the protection strip extends along a periphery of a substrate, particularly a printed circuit board, which substrate carries the electronic circuit.

Further, particularly, according to an embodiment the protection strip may comprise two opposing ends, wherein the respective end is in electrical contact with a sleeve that protrudes through a through hole of the housing out of internal space of the housing, wherein particularly the through hole is formed by a first and a second recess, wherein the first recess is formed in the boundary area of the first housing part, and wherein the second recess is formed in the boundary area of the second housing part.

According to an embodiment of the present invention, the sleeve is configured as a feedthrough flange which is welded to the housing. The sleeve can for instance be configured to contain the connection pin and/or guide an antenna of the assembly, e.g. a silicone antenna.

Furthermore, according to an embodiment of the assembly according to the present invention, the housing or the housing parts is/are formed out of or comprises titanium.

Furthermore, according to an embodiment of the assembly according to the present invention, the protection strip is formed out of or comprises metal alloy material, for instance constantan.

Furthermore, according to an embodiment of the assembly according to the present invention, the ground connection (e.g. ground connection pad on substrate/PCB of electronic circuit) is formed out of or comprises metal alloy material, for instance constantan.

According to an embodiment of the present invention, the protection strip and the ground connection are made of similar materials in order to allow connecting them via a welding process (e.g. laser welding).

Yet another aspect of the present invention relates to a method for producing an assembly, particularly an assembly according to the present invention.

With the foregoing and other objects in view there is provided, in accordance with the invention, a method which comprises the steps of:
a) providing a first and a second housing part, an electronic circuit, and a protection strip,
b) mounting the protection strip to the first housing part, so that the protection strip is in electrical contact with the first housing part,
c) arranging the electronic circuit in an internal space of the first housing part,
d) establishing an electrical connection between the electronic circuit and the protection strip,
e) arranging the second housing part on the first housing part, and
f) connecting the first housing part to the second housing part so as to form a housing which hermetically seals said electronic circuit.

Furthermore, according to an embodiment of the method according to the present invention, establishing the electrical connection between the electronic circuit and the protection strip comprises the steps of: bending a wing of the protection strip towards a ground connection (e.g. ground connection pad, see above) of the electronic circuit, which wing particularly protrudes from an elongated portion of the protection strip that extends along a circumferential boundary area of the first housing part, and connecting, particularly welding, the wing to the ground connection so that the wing stands in electrical contact with the ground connection of the electronic circuit.

Furthermore, according to an embodiment of the method according to the present invention, the protection strip is arranged along the boundary area of the first housing part on an inside of the first housing part so that the protection strip protrudes past the boundary area of the first housing part, particularly so as to be able to also overlap with the boundary area of the second housing part once the second housing part is arranged on the first housing part so that their boundary areas are arranged on one another.

Furthermore, according to an embodiment of the method according to the present invention, the protection strip is welded to the first housing part, particularly to the boundary area of the first housing part. Laser welding can be applied to weld the protection strip to the boundary area of the first housing part.

Furthermore, according to an embodiment of the method according to the present invention, the second housing part comprises a circumferential boundary area, wherein the circumferential boundary area of the second housing part is welded to the circumferential boundary area of the first housing part to form a housing that encloses the electronic circuit, wherein the protection strip protects the electronic circuit upon welding of the first housing part to the second housing part.

Integrating the ground contact into the welding protection strip saves installation space, which may be used to reduce the overall size of the assembly/housing or may provide additional space for electrical components. FIG. 4 shows the free installation space in case of a medical monitoring device. The usual ground connection (e.g. pin) according to the prior art would be located in the space marked by the ellipse. This space can now be used completely by other components. Furthermore, the additional wing of the protection strip almost constitutes no extra cost since the basic shape is realized using a cutting, etching or pressing process. Furthermore, a wiring band can be omitted that would be needed to connect said pin to the ground connection of the circuit.

Other features which are considered as characteristic for the invention are set forth in the appended claims.

Although the invention is illustrated and described herein as embodied in a ground contact integrated into a welding protection strip, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
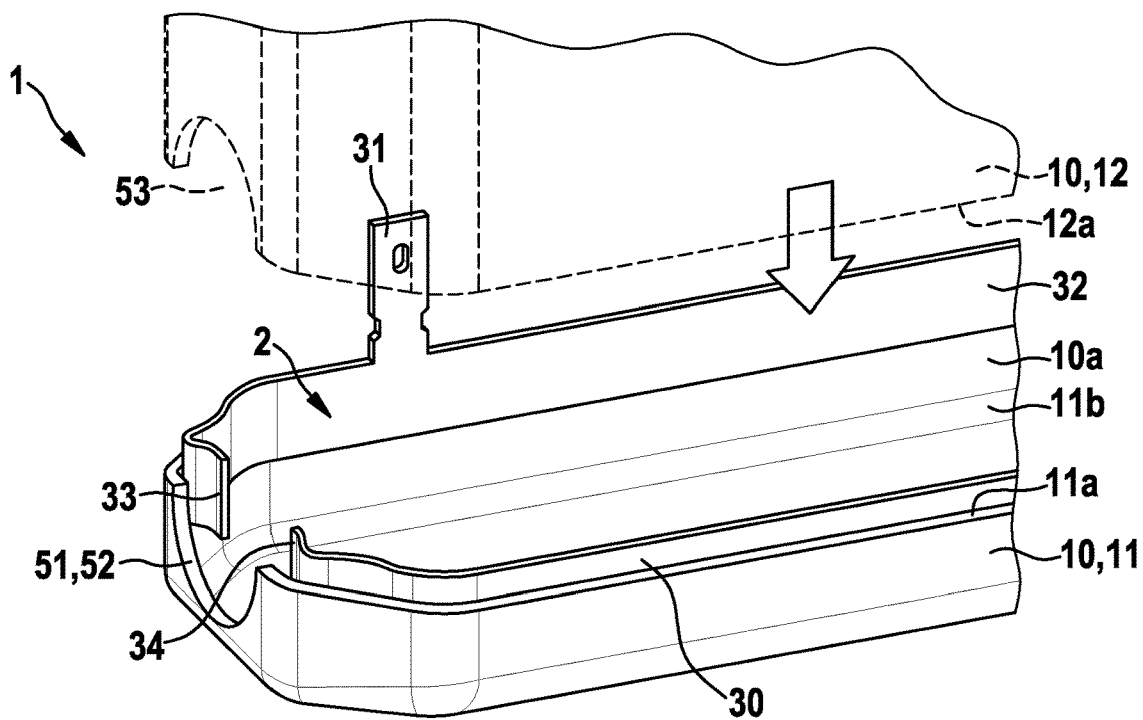
FIG. 1 is a diagrammatic, perspective view of a first (lower) and a second (upper) housing part of a housing of an assembly according to the present invention as well as a protection strip connected to the first housing part.
Figure 2:
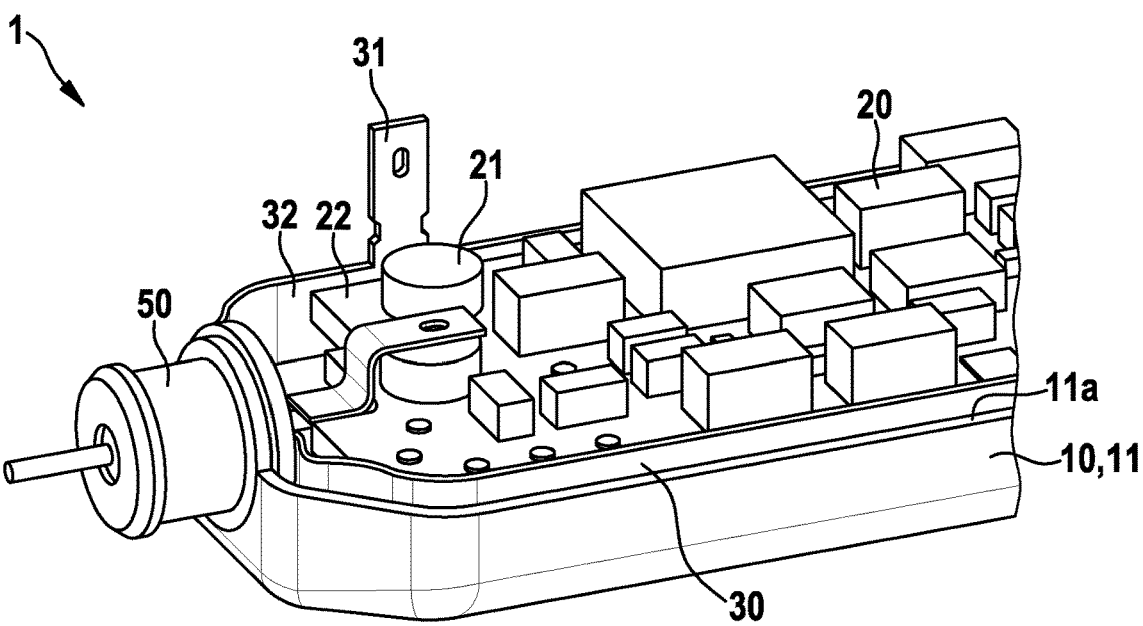
FIG. 2 is a perspective view of the first housing part of FIG. 1 and an electronic circuit arranged in the first housing part, wherein a wing of the protection strip protrudes upwards.
Figure 3:
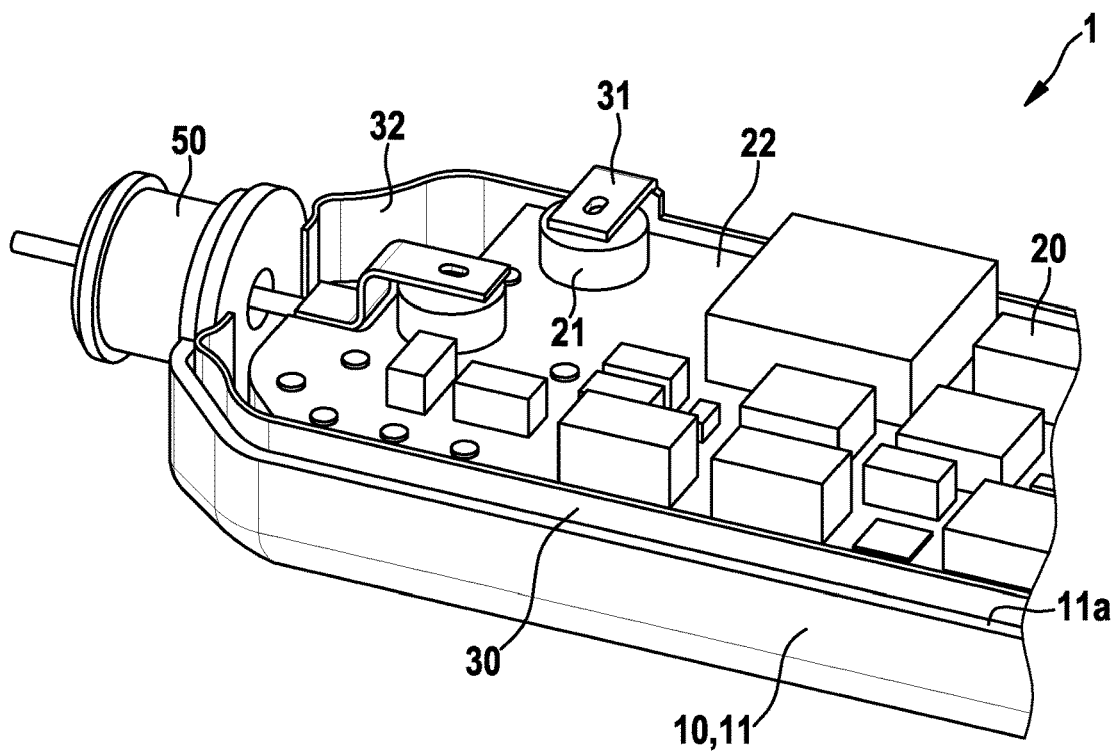
FIG. 3 is a perspective view of the assembly of FIG. 2 with the wing bent downwards onto a ground connection of the electronic circuit.
Figure 4:
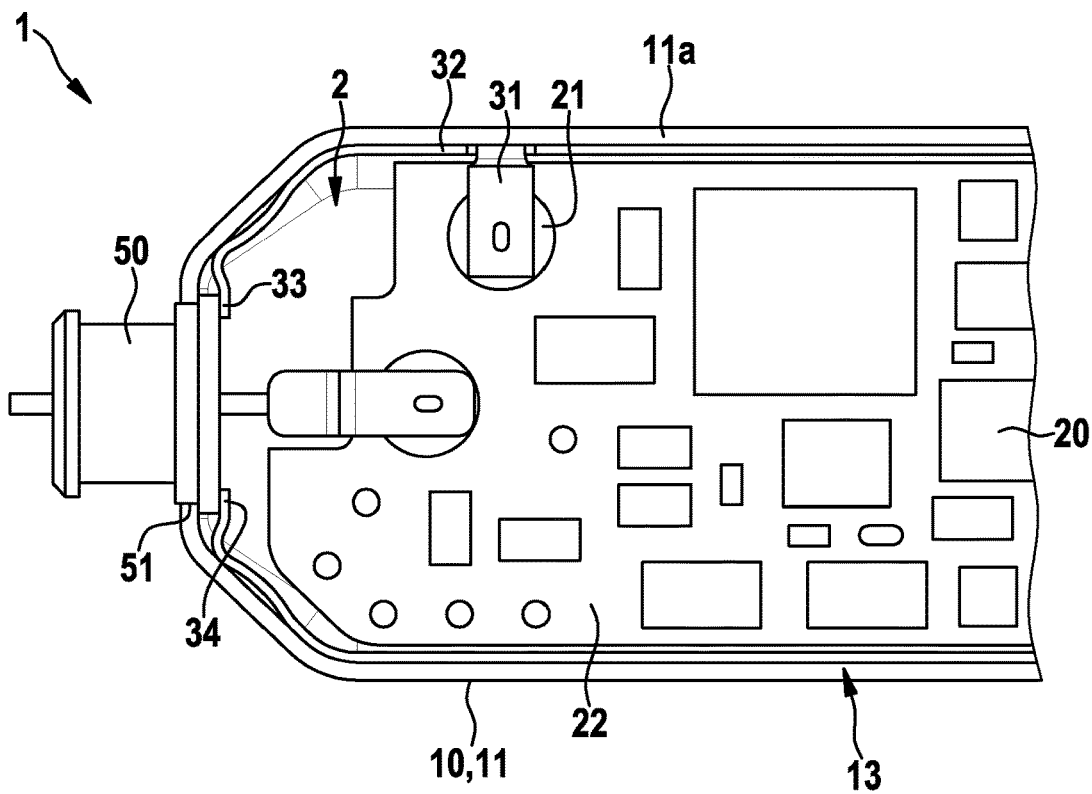
FIG. 4 is a top view of the assembly shown in FIGS. 1 to 3.

Referring now to the figures of the drawings in detail and first, particularly to FIG. 1 thereof, there is shown in conjunction with FIGS. 2 to 4 an assembly 1 according to the present invention. The assembly 1 comprises a housing 10 (FIG. 1 indicates the two housing parts 11, 12 forming housing 10), which housing 10 defines/encloses an internal space 2 of the assembly 1. The assembly 1 further comprises an electronic circuit 20 arranged in the internal space 2, and a protection strip 30 arranged in the internal space 2 for protecting the electronic circuit 20 against external influences. According to the present invention, the protection strip 30 forms a ground conductor that is electrically connected to the housing 10 and to a ground connection 21 of the electronic circuit 20.

Particularly, the electronic circuit 20 is arranged on a substrate 22, here in the form of a printed circuit board, wherein the ground connection 21 is formed as a pad 21 arranged on the substrate 22.

As indicated in FIG. 1, the housing 10 comprises two housing parts 11, 12, here e.g. formed as shells 11, 12, wherein each housing part 11, 12 comprises a circumferential boundary area 11a, 12a, which boundary areas 11a, 12a are to be connected by a welding seam 13 which may be generated using laser welding. The position of the seam 13 is indicated in FIG. 4. Particularly, the protection strip 30 is configured to protect the electronic circuit 20 against external influences such as heat and welding material splatter generated upon welding of the welding seam 13.

In order to protect the circuit 20, the protection strip 30 is particularly arranged such in the housing 10 that it extends around the periphery of the substrate 22 of the electric circuit 20. The protection strip 30 overlaps both boundary areas 11a, 12a of the housing parts 11, 12 and thus covers a gap between these boundary areas 11a, 12a from an inside 10a of the housing 10 when the boundary areas 11a, 12a are arranged on one another (e.g. by lowering the second housing part 12 down to the first housing part 11 as indicated by the arrow in FIG. 1). This position of the protection strip 30 can be achieved by connecting, particularly welding, the protection strip 30 to the first housing part 11 such that it protrudes beyond the boundary area 11a of the first housing part 11 as shown in FIG. 1.

For electrically contacting the ground connection 21 of the electronic circuit 21, the protection strip 30 comprises a wing 31 that protrudes from a portion 32 of the protection strip 30 that extends along the circumferential boundary area 11a of the first housing part 11. This wing is bent downwards (see FIGS. 2 and 3) and is then connected, particularly welded, to the ground connection 21 of the electronic circuit 20 so that the wing 31 stands in electrical contact with the ground connection 21.

Further, additionally, as shown in FIGS. 1 to 4 the protection strip 30 may comprise two opposing ends 33, 34. A respective end 33, 34 is in electrical contact with a sleeve 50 that protrudes through a through hole 51 of the housing 10 out of internal space 2 of the housing 10. The through hole 51 is formed by a first recess 52 and a second recess 53. The first recess 52 is formed in the boundary area 11a of the first housing part 10, and the second recess 53 is formed in the boundary 12a area of the second housing part. When the two housing parts 11, 12 are connected to each other the two recesses 52, 53 meet and form the through hole 51 for the sleeve 50.

Integrating the ground conductor into the protection strip 30 as described herein frees installation space as indicated in FIG. 4 by the ellipse. This additional installation space can be used for further electrical components. Alternatively, the overall size of the housing 10 can be reduced.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. An implantable medical device, comprising:
    a housing defining an internal space of the implantable medical device, said housing having two housing parts, each of said housing parts having a circumferential boundary area, the circumferential boundary areas are connected to each other and form said housing;
    an electronic circuit disposed in said internal space and having a ground connection, said housing hermetically sealing said electronic circuit; and
    a protection strip disposed in said internal space for protecting said electronic circuit against external influences, said protection strip forming a ground conductor that is electrically connected to said housing and to said ground connection of said electronic circuit, said protection strip extending substantially along a whole length of the circumferential boundary area, and said protection strip being formed in one piece.

2. The medical device according to claim 1, wherein said housing parts are connected to each other via a welding seam that connects said circumferential boundary areas to one another.

3. The medical device according to claim 2, wherein said protection strip is configured to protect said electronic circuit against the external influences generated upon welding of said welding seam.

4. The medical device according to claim 1, wherein said protection strip is disposed in said internal space such that said protection strip overlaps with both said circumferential boundary areas on an inside of said housing, and said inside of said housing faces said electronic circuit.

5. The medical device according to claim 1, wherein said protection strip comprises a wing protruding from a portion of said protection strip that extends along the circumferential boundary area of a first of said housing parts, said wing is connected to said ground connection of said electronic circuit so that said wing stands in electrical contact with said ground connection.

6. The medical device according to claim 1, further comprising a substrate, said protection strip extends along a periphery of said substrate and said substrate carries said electronic circuit.

7. The medical device according to claim 1, wherein said housing is formed out of or comprises titanium.

8. The medical device according to claim 1, wherein said protection strip is formed out of or comprises a metal alloy material.

9. The medical device according to claim 1, wherein said ground connection is formed out of or comprises a metal alloy material.

10. The medical device according to claim 1, wherein said housing parts are shells.

11. The medical device according to claim 6, wherein said substrate is a printed circuit board.

12. A method for producing an implantable medical device, which comprises the steps of:
    providing a first and a second housing part each having a circumferential boundary area, the first and the second housing part defining an internal space of the implantable medical device, an electronic circuit, and a protection strip;
    mounting the protection strip to the first housing part so that the protection strip is in electrical contact with the first housing part, the protection strip extending along a whole length of the circumferential boundary area, and the protection strip is formed in one piece;
    disposing the electronic circuit in an internal space of the first housing part;
    forming an electrical connection between the electronic circuit and the protection strip;

disposing the second housing part on the first housing part; and connecting the first housing part to the second housing part so as to form a housing which hermetically encloses the electronic circuit.

13. The method according to claim 12, wherein the step of forming the electrical connection between the electronic circuit and the protection strip comprises the further steps of:

bending a wing of the protection strip towards a ground connection of the electronic circuit; and connecting the wing to the ground connection so that the wing stands in electrical contact with the ground connection.

14. The method according to claim 12, wherein:

the first housing part comprises a circumferential boundary area; and the protection strip is disposed along the circumferential boundary area of the first housing part on an inside of the first housing part so that the protection strip protrudes beyond the circumferential boundary area of the first housing part.

15. The method according to claim 14, which further comprises welding the protection strip to the first housing part.

16. The method according to claim 14, wherein:

the second housing part comprises a circumferential boundary area;

the circumferential boundary area of the second housing part is welded to the circumferential boundary area of the first housing part to form the housing that encloses the electronic circuit; and the protection strip protects the electronic circuit upon welding of the first housing part to the second housing part.

17. An implantable medical device, comprising:

a housing defining an internal space of the implantable medical device, said housing having two housing parts, each of said housing parts having a circumferential boundary area, the circumferential boundary areas are connected to each other and form said housing, said housing parts being connected to each other via a welding seam that connects the circumferential boundary areas to one another;

an electronic circuit disposed in said internal space and having a ground connection, said housing hermetically sealing said electronic circuit; and a protection strip disposed in said internal space for protecting said electronic circuit against external influences, said protection strip forming a ground conductor that is electrically connected to said housing and to said ground connection of said electronic circuit, said protection strip configured to protect said electronic circuit against the external influences generated upon welding of said welding seam, said protection strip extending along a whole length of the circumferential boundary area, and said protection strip being formed in one piece.

18. An implantable medical device, comprising:

a housing defining an internal space of the implantable medical device and having a through hole formed therein;

a sleeve protruding through said through hole of said housing and out of said internal space of said housing;

an electronic circuit disposed in said internal space and having a ground connection, said housing hermetically sealing said electronic circuit; and a protection strip disposed in said internal space for protecting said electronic circuit against external influences, said protection strip forming a ground conductor that is electrically connected to said housing and to said ground connection of said electronic circuit, wherein said protection strip having two opposing ends, wherein a respective end of said two opposing ends is in electrical contact with said sleeve, said protection strip extending along a whole length of a circumferential boundary area of said housing, and said protection strip being formed in one piece.

* * * * *